United States Patent [19]

McArthur et al.

[11] 3,965,260

[45] June 22, 1976

[54] ANTI-INFLAMMATORY DIPEPTIDE

[75] Inventors: John N. McArthur, Toronto, Canada; Peter D. Dawkins, Taunton; Mervyn J. H. Smith, London, both of England

[73] Assignee: John N. McArthur, Toronto, Canada

[22] Filed: July 7, 1975

[21] Appl. No.: 593,672

[52] U.S. Cl. .............................. 424/177; 424/317
[51] Int. Cl.² ........................................ A61K 37/00
[58] Field of Search ............................ 424/177, 319

[56] References Cited
OTHER PUBLICATIONS

Chem. Abst., 67–32925e (1967).
Chem. Abst., 68–92930h (1968).
Chem. Abst., 73–106061t (1970).

*Primary Examiner*—Stanley J. Friedman

[57] ABSTRACT

The pharmaceutical composition has a dipeptide or a pharmaceutically-acceptable salt thereof as an active ingredient. The depeptide has the general formula

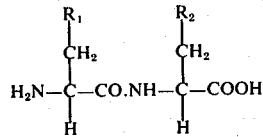

wherein $R_1$ and $R_2$ are the same or different and each is either phenyl or indolyl. administration composition may be in a solid form for oral administraion in which case the active ingredient is surrounded by an enteric coating. The composition may also be in a liquid form for administration by injection in which case the active ingredient is dissolved in a physiologically compatible sterile liquid. The composition is useful in the treatment of inflammation in mammals and may be administered daily in an amount of about 40mg of the dipeptide or salt per kilogram weight of the mammal.

13 Claims, No Drawings

ANTI-INFLAMMATORY DIPEPTIDE

The present invention relates generally to pharmaceutical compositions useful in the treatment of rheumatism and other disorders involving inflammation and to a method of use thereof. More particularly the invention is concerned with a composition having anti-inflammatory properties and being in a solid form for oral administration or in a liquid form for administration by injection. The composition has as active ingredient a dipeptide or its pharmaceutically-acceptable salt, which dipeptide has the general formula:

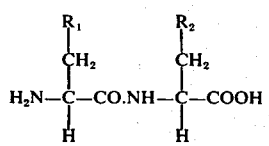

in which $R_1$ and $R_2$ are the same or different and each is either phenyl or indolyl. When the composition is in a solid form the active ingredient is surrounded by an enteric coating and when the composition is in a liquid form is dissolved in a physiologically compatible sterile liquid. The invention is also particularly concerned with a method of administration of said composition in the relief or treatment of rheumatism and other disorders involving inflammation.

Many agents have been proposed for the relief or treatment of rheumatism and other disorders involving inflammation but many of them either involve serious toxicity problems or are not very effective anti-inflammatory agents or suffer from both disadvantages.

It has been found that a pharmaceutical composition comprising an enteric coated tablet, capsule, lozenge or pill or a solution containing a dipeptide of the formula set out above or its pharmaceutically-acceptable salt possesses effective anti-inflammatory properties for the relief or treatment of inflammation and the accompanying swelling in warm-blooded mammals.

For the sake of convenience, the dipeptide present in the pharmaceutical composition of the invention is referred to as "the dipeptide". Each of the amino acids which constitute the dipeptide are either phenylalanine or tryptophan. The amino acids may have either D- or L- stereoisomeric form. There are therefore sixteen compounds covered by the formula given above, and any form can be used although not all forms produce identical results. Mixtures of the compounds may also be used in the composition. Some dipeptides (especially those containing the L-form) tend to be more quickly metabolized and hence have a shorter biological half life than the dipeptides which contain the amino acids of the D-stereoisomer. As a result dipeptides containing the L-form are generally effective for a shorter period of time than the dipeptides containing the D-form. Examples of the latter dipeptides are D-phenylalanyl-D-phenylalanine, D-phenylalanyl-D-tryptophan, D-tryptophanyl-D-phenylalanine and D-tryptophanyl-D-tryptophan, all of which resist rapid hydrolysis by mammalian plasma and tissue peptidases with the result that they have a long half life, for example 6 hours or more.

Dipeptides which contain L-tryptophan have a double barrelled effect; they are anti-inflammatories before metabolism and anti-depressants thereafter. The level of L-tryptophan in the dipeptide and the quantity of dipeptide administered can usefully be adjusted according to the level of depression of the patient (as determined on the Hamilton Depression Scale, Hamilton, M. (1960), J.Neurol Neurosurg. Physchiat, 23,56). For example, L-tryptophanyl-L-tryptophan can usefully be administered to a severely depressed patient suffering from rheumatoid arthritis. The patient will experience rapid relief from both inflammation and depression although the relief from inflammation will be more short lived than where the patient is given D-forms of the dipeptide. A less severely depressed patient might usefully be given a formulation containing a smaller proportion of L-tryptophanyl-L-tryptophan, e.g. a formulation containing 10% down to as little as 1% of L-tryptophanyl-L-tryptophan based on the total weight of dipeptides present in the formulation. A patient given the latter formulation will experience a lower level of anti-depression activity and more long-lasting relief from inflammation. A patient who is not depressed can usefully be given a formulation containing only amino acids of the D-stereoisomeric form. Accordingly, the condition of the patient will dictate which form of dipeptide can most usefully be administered to him.

The dipeptides may be made by conventional methods, for example, by reaction between

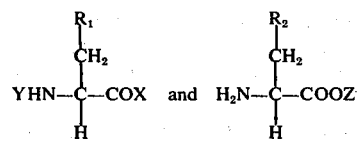

where Y and Z are protective groups that may be removed after completion of the reaction, and X is a halogen atom, e.g. chlorine. If the reaction is between two molecules of the same acid, then Z may also be hydrogen. For example, Y may be the carbobenzoxyl radical ($C_6H_5CH_2OCO-$) and Z may be a methyl group. However, any suitable method used in peptide synthesis may be employed, for example, generally as described in "The Chemistry of Amino Acids and Proteins" edited by C. L. A. Schmidt, 2nd edition, 1945, Charles T. Thomas, publisher, Springfield, Illinois, p. 262.

The term "pharmaceutically-acceptable salt" as used herein includes any salt which is not substantially more toxic than an equal weight of the dipeptide from which it is derived when measured in the same mammalian host using the same vehicle and method of administration. Some examples of such salts are the sodium, potassium, calcium, ammonium and 2 hydroxyethylammonium. The preferred salts are the pharmaceutically-acceptable salts with an alkali metal, an alkaline earth metal, ammonia or an amine.

In accordance with the invention, the dipeptide or a pharmaceutically-acceptable salt thereof is formulated into solid pharmaceutical compositions in dosage unit form for oral administration or into liquid compositions also in dosage unit form for administration by injection. In the former case, the dipeptide or its salt is coated with an enteric substance, i.e. one which resists dissolution in gastric fluids but disintegrates and releases the active ingredient in the intestine. Enteric substances suitable for the purpose are fats, fatty acids, waxes and mixtures, shellac, ammoniated shellac and cellulose acetate phthalate. Shellac and cellulose acetate phthalate are preferred enteric coating substances.

The dipeptide or its salt is only effective as an antiinflammatory where it reaches the intestine intact or substantially intact and the enteric coating is necessary to ensure that it does so. Should the active ingredient not be protected by an enteric coating, it will be dissolved by the gastric fluids in the stomach and will be ineffective as an antiinflammatory. Preferably, as a further protection to the active ingredient, it is combined prior to enteric coating with approximately 30% by weight albumin which also resists degradation in the stomach. Formulation of the dipeptide or its pharmaceutically-acceptable salt into a liquid composition involves dispersing the dipeptide or its salt in a liquid which is physiologically compatible sterile and which is a solublizer therefor. A suitable liquid is distilled water raised to a pH of 12 or higher with a base such as sodium hydroxide. After dissolution of the dipeptide or salt, an acid such as hydrochloric acid can be added to decrease the pH of the resulting solution to about 7.2 at which the solution is suitable for injection.

The solid or liquid composition containing the dipeptide or its salt can be formulated in dosage unit form with a pharmaceutical carrier and also, if desired, a suitable additive such as a bacteriostat. Some examples of dosage unit forms are tablets, capsules, lozenges and pills; as well as powders and aqueous and non-aqueous solutions packaged on containers either one or some large number of dosage units and capable of being subdivided into individual doses by suitable measuring devices.

Examples of pharmaceutical carriers suitable for use in association with the dipeptide or its pharmaceutically-acceptable salt includes sugars such as lactose and sucrose; starches such as corn starch and potato starch; cellulose derivatives such as sodium carboxymethyl cellulose, ethyl cellulose, methyl cellulose, and cellulose acetate phthalate; talc; stearic acid; magnesium stearate; vegetable oils such as peanut oil, cottonseed oil, sesame oil, olive oil, corn oil and oil of theobroma; propylene glycol; glycerine; sorbital; polyethylene glycol; water; agar; alginic acid; isotonic saline; and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the dipeptide or its pharmaceutically-acceptable salt in the foregoing composition can be varied within wide limits but for practical purposes it is preferably present in a concentration of at least 5 percent. The most satisfactory compositions are those in which a much higher proportion of said dipeptide or its pharmaceutically-acceptable salt is present. In cases where the composition of the invention is to be administered to humans, it should preferably contain from 25 to 1,000 mg of said dipeptide or its pharmaceutically-acceptable salt per dosage unit so that the entire amount to be administered during a day can be made up from a reasonable number of dosage units.

Also in accordance with the invention, the composition comprising the dipeptide or its pharmaceutically-acceptable salt and a suitable pharmaceutical carrier are employed as an anti-inflammatory agent. To this end they are administered in dosage unit form for the relief and the treatment of rheumatism and other disorders involving inflammation. The composition can be administered orally with the dose adjusted to the needs and tolerances of the individual patients. A suitable daily dose for mammals is about 40 mg/kg., i.e. 40 mg of dipeptide or its salt per kg of patient weight. The composition may, for example, be packed in a cachet, the cachet body then serving as a solid carrier. Alternatively, the dipeptide or its pharmaceutically-acceptable salt dissolved in a physiologically compatible sterile solution can be administered by injection. Such solutions may contain a thickening agent, for example, methyl cellulose. Thus, for example, a sterile solution of 50 mg of dry sterile dipeptide in powder form dissolved in 10 ml water containing 1% weight by volume methyl cellulose may be prepared and may be packed in sealed containers. The solution, in proper doses, may subsequently be administered by injection.

What we claim is:

1. A method for the treatment of inflammation in a mammal which comprises administering to such mammal an effective amount of a composition comprising: a dipeptide or a pharmaceutically-acceptable salt thereof surrounded by a coating of an enteric substance which resists dissolution in gastric fluids but disintegrates in the intestine, said dipeptide having the general formula:

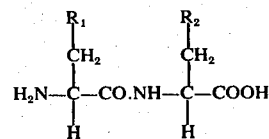

wherein $R_1$ and $R_2$ are the same or different and each is either phenyl or indolyl.

2. A method for the treatment of inflammation in a mammal which comprises administering to such mammal an effective D-phenylalanyl-D-tryptophan, of a composition comprising: a dipeptide or a pharmaceutically-acceptable salt thereof dissolved in a physiologically compatible sterile liquid, said dipeptide having the general formula:

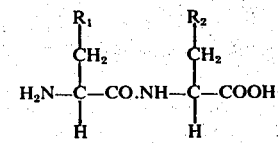

wherein $R_1$ and $R_2$ are the same or different and each is either phenyl or indolyl.

3. A method as claimed in claim 1 wherein the daily dose of said composition administered to said mammal is about 40 mg of said dipeptide or pharmaceutically-acceptable salt thereof per kilogram weight of said mammal.

4. A method as claimed in claim 2 wherein the daily dose of said composition administered to said mammal is about 40 mg of said dipeptide or pharmaceutically-acceptable salt thereof per kilogram weight of said mammal.

5. A method as claimed in claim 1 wherein said dipeptide is selected from the group consisting of: D-phenylalanyl-D-phenylalanine, D-phenylalanyl-D-tryptophan, D-tryptophany-D-phenylalanine, D-tryptophanyl-D-tryptophan and L-tryptophanyl-L-tryptophan and mixtures thereof.

6. A method as claimed in claim 2 wherein said dipeptide is selected from the group consisting of: D-phenylalanyl-D-phenylalanine, D-p henylalanyl-D-tryptophan, D-tryptophanyl-D-phenylalanine, D-tryptophanyl-D-tryptophan and L-tryptophanyl-L-tryptophan, L-tryptophanyl-D-tryptophan and mixtures thereof.

7. A pharmaceutical composition useful in the treatment of inflammation which comprises: a dipeptide or a pharmaceutically-acceptable salt thereof surrounded by a coating of an enteric substance which resists dissolution in gastric fluids but disintegrates in the intestine, the amount of said dipeptide present in said composition being an amount effective against inflammation, said dipeptide having the general formula:

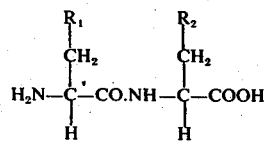

wherein $R_1$ and $R_2$ are the same or different and each is either phenyl or indolyl.

8. The composition as claimed in claim 7 wherein said enteric coating is shellac or cellulose acetate phthalate.

9. The composition of claim 7 wherein said dipeptide is selected from the group consisting of: D-phenylalanyl-D-phenylalanine, D-phenylalanyl-D-tryptophan, D-tryptophanyl-D-phenylalanine, D-tryptophanyl-D-tryptophan, and L-tryptophanyl-L-tryptophan.

10. A pharmaceutical composition useful in the treatment of inflammation which comprises: a dipeptide or a pharmaceutically-acceptable salt thereof dissolved in a physiologically compatible sterile liquid, the amount of said dipeptide present in said composition being an amount effective against inflammation, said dipeptide having the general formula:

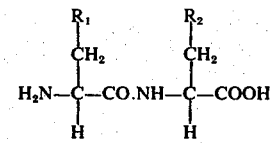

wherein $R_1$ and $R_2$ are the same or different and each is either phenyl or indolyl.

11. The composition of claim 10 wherein said dipeptide is selected from the group consisting of: D-phenylalanyl-D-phenylalanine, D-phenylalanyl-D-tryptophan, D-tryptophanyl-D-phenylalanine, D-tryptophanyl-D-tryptophan, L-tryptophanyl-L-tryptophan and mixtures thereof.

12. The composition of claim 10 wherein said sterile liquid is water to which is added a base to cause dissolution of said active ingredient and afterward to which is added an acid to decrease the pH to about 7.2.

13. The composition of claim 12 wherein said base is sodium hydroxide and said acid is hydrochloric acid.

* * * * *